(12) United States Patent
Kwon et al.

(10) Patent No.: US 12,059,273 B2
(45) Date of Patent: Aug. 13, 2024

(54) APPARATUS AND METHOD FOR ESTIMATING BIO-INFORMATION

(71) Applicant: SAMSUNG ELECTRONICS CO., LTD., Suwon-si (KR)

(72) Inventors: Ui Kun Kwon, Hwaseong-si (KR); Chang Soon Park, Chungju-si (KR); Seung Keun Yoon, Seoul (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1043 days.

(21) Appl. No.: 16/843,104

(22) Filed: Apr. 8, 2020

(65) Prior Publication Data

US 2021/0085259 A1     Mar. 25, 2021

(30) Foreign Application Priority Data

Sep. 19, 2019    (KR) .................. 10-2019-0115511

(51) Int. Cl.
    *A61B 5/00*            (2006.01)
    *A61B 5/02*            (2006.01)
    (Continued)

(52) U.S. Cl.
    CPC ........ *A61B 5/7278* (2013.01); *A61B 5/02007* (2013.01); *A61B 5/02116* (2013.01);
    (Continued)

(58) Field of Classification Search
    CPC .... A61B 5/02007; A61B 5/021–02125; A61B 5/024; A61B 5/02438; A61B 5/681;
    (Continued)

(56) References Cited

U.S. PATENT DOCUMENTS

| | | |
|---|---|---|
| 6,602,198 B2 | 8/2003 | Yokozeki |
| 6,758,822 B2 | 7/2004 | Romano |

(Continued)

FOREIGN PATENT DOCUMENTS

| | | |
|---|---|---|
| CN | 107638166 A | 1/2018 |
| CN | 107837078 A | 3/2018 |

(Continued)

OTHER PUBLICATIONS

Communication dated Oct. 14, 2020, issued by the European Patent Office in counterpart European Application No. 20174375.4.

(Continued)

*Primary Examiner* — Navin Natnithithadha
*Assistant Examiner* — Alice Ling Zou
(74) *Attorney, Agent, or Firm* — Sughrue Mion, PLLC

(57) ABSTRACT

Provided is an apparatus for estimating bio-information. The apparatus for estimating bio-information according to an embodiment includes a processor configured to obtain a pulse wave signal from a user; extract components of a plurality of element waveforms which constitute a waveform of the pulse wave signal; and obtain a cardiovascular feature based on the extracted components of the plurality of element waveforms. The processor is configured to extract a component of at least one element waveform based on a component of an adjacent element waveform.

13 Claims, 13 Drawing Sheets

(51) Int. Cl.
  *A61B 5/021* (2006.01)
  *A61B 5/024* (2006.01)
  *A61B 5/16* (2006.01)

(52) U.S. Cl.
  CPC .......... *A61B 5/02125* (2013.01); *A61B 5/024* (2013.01); *A61B 5/165* (2013.01); *A61B 5/681* (2013.01); *A61B 5/6898* (2013.01)

(58) Field of Classification Search
  CPC ...... A61B 5/6898; A61B 5/7235–7239; A61B 5/7278; A61B 5/02416; A61B 5/6843–6844
  See application file for complete search history.

(56) References Cited

U.S. PATENT DOCUMENTS

| | | | |
|---|---|---|---|
| 10,667,757 | B2 | 6/2020 | Park et al. |
| 10,820,858 | B2 | 11/2020 | Yoon et al. |
| 11,123,022 | B2 | 9/2021 | Kwon et al. |
| 11,382,572 | B2 | 7/2022 | Park et al. |
| 11,666,277 | B2 | 1/2023 | Yoon et al. |
| 2005/0283086 | A1* | 12/2005 | Satoh ............ A61B 5/022 600/490 |
| 2008/0214942 | A1 | 9/2008 | Oh et al. |
| 2010/0210956 | A1 | 8/2010 | Im |
| 2011/0208073 | A1* | 8/2011 | Matsukawa ........ A61B 5/6822 600/508 |
| 2012/0226174 | A1* | 9/2012 | Ikeda ............ A61B 5/02125 600/500 |
| 2013/0324859 | A1 | 12/2013 | Park et al. |
| 2014/0163632 | A1 | 6/2014 | Ghosh et al. |
| 2016/0038037 | A1* | 2/2016 | Kovacs ............ A61B 5/742 600/301 |
| 2016/0051193 | A1* | 2/2016 | Park ............ A61B 5/02438 600/300 |
| 2016/0128582 | A1 | 5/2016 | Chod et al. |
| 2017/0337414 | A1* | 11/2017 | Ohno ............ G06V 40/1365 |
| 2017/0360314 | A1 | 12/2017 | Proenca et al. |
| 2018/0020990 | A1 | 1/2018 | Park et al. |
| 2018/0078215 | A1* | 3/2018 | Park ............ A61B 5/021 |
| 2018/0096119 | A1* | 4/2018 | Yun ............ A61B 5/024 |
| 2018/0132731 | A1 | 5/2018 | Albadawi et al. |
| 2018/0177465 | A1* | 6/2018 | Kwon ............ A61B 5/316 |
| 2019/0110757 | A1 | 4/2019 | Kwon et al. |
| 2020/0245952 | A1 | 8/2020 | Park et al. |
| 2021/0100456 | A1 | 4/2021 | Park et al. |
| 2021/0137425 | A1* | 5/2021 | Ajima ............ A61B 5/14546 |
| 2021/0378602 | A1 | 12/2021 | Kwon et al. |
| 2022/0117563 | A1 | 4/2022 | Park et al. |
| 2022/0287655 | A1 | 9/2022 | Park et al. |
| 2023/0038983 | A1 | 2/2023 | Park et al. |

FOREIGN PATENT DOCUMENTS

| | | | | |
|---|---|---|---|---|
| CN | 107928643 | A | | 4/2018 |
| CN | 108354597 | A | | 8/2018 |
| CN | 108814591 | A | | 11/2018 |
| CN | 108937878 | A | | 12/2018 |
| CN | 109480800 | A | | 3/2019 |
| EP | 3381369 | A1 | * | 10/2018 .......... A61B 5/0059 |
| JP | 2002-136487 | A | | 5/2002 |
| JP | 2014-64667 | A | | 4/2014 |
| KR | 10-1298838 | B1 | | 8/2013 |
| KR | 10-2016-0007052 | A | | 1/2016 |
| KR | 10-2018-0010062 | A | | 1/2018 |
| KR | 1020190043453 | A | | 4/2019 |
| WO | 2014/162360 | A1 | | 10/2014 |

OTHER PUBLICATIONS

Communication dated Dec. 13, 2022 issued by the Korean Patent Office in application No. 10-2019-0115511.
Office Action dated Jan. 29, 2024, issued by Chinese Patent Office in Chinese Patent Application No. 202010254606.3.

* cited by examiner

APPARATUS AND METHOD FOR ESTIMATING BIO-INFORMATION

CROSS-REFERENCE TO RELATED APPLICATION(S)

This application is based on and claims priority under 35 U.S.C. § 119 to Korean Patent Application No. 10-2019-0115511, filed on Sep. 19, 2019, in the Korean Intellectual Property Office, the disclosure of which is incorporated by reference herein in its entirety.

BACKGROUND

1. Field

The disclosure relates to technology for non-invasively estimating bio-information.

2. Description of Related Art

Recently, with the aging population, soaring medical costs, and a lack of medical personnel for specialized medical services, research is being actively conducted on information technology (IT)-medical convergence technologies, in which IT and medical technology are combined. Particularly, monitoring of the health condition of the human body is not limited to medical institutions, and is expanding to mobile healthcare fields that may monitor a user's health condition anywhere and anytime in daily life such as at home, at the office, etc. Typical examples of bio-signals, which indicate the health condition of individuals, include an electrocardiography (ECG) signal, a photoplethysmogram (PPG) signal, an electromyography (EMG) signal, and the like, and various bio-signal sensors have been developed to measure these signals in daily life. Particularly, a PPG sensor may estimate blood pressure of a human body by analyzing a shape of pulse waves which reflect cardiovascular status, and the like.

SUMMARY

Additional aspects will be set forth in part in the description which follows and, in part, will be apparent from the description, or may be learned by practice of the presented embodiments.

According to an aspect of the disclosure, an apparatus for estimating bio-information may include a processor configured to obtain a pulse wave signal from a user; extract components of a plurality of element waveforms which constitute a waveform of the pulse wave signal; and obtain a cardiovascular feature based on the extracted components of the plurality of element waveforms. The processor may be configured to extract a component of at least one element waveform based on a component of an adjacent element waveform.

The components of the plurality of element waveforms may include a time and an amplitude of a first element waveform related to a propagation wave, and a time and an amplitude of a second element waveform related to a reflection wave.

The cardiovascular feature may include a ratio between the amplitude of the first element waveform and the amplitude of the second element waveform.

The processor may be configured to extract times of the plurality of element waveforms based on at least one of a differential signal of the pulse wave signal and a predetermined fixed value.

The processor may be configured to extract an amplitude of each element waveform based on an amplitude of the pulse wave signal which corresponds to a time of each element waveform.

The processor may subtract a predetermined percentage of an amplitude of the pulse wave signal corresponding to the adjacent element waveform from an amplitude of the pulse wave signal corresponding to the at least one element waveform, and obtain an amplitude of the at least one element waveform.

The predetermined percentage is a general value obtained from a plurality of users or a personalized value obtained from a specific user in a stable state.

The processor may obtain a second-order differential signal of the pulse wave signal, and extract the components of the plurality of element waveforms by analyzing a local minimum point or a local maximum point of a waveform of the obtained second-order differential signal.

The processor may extract times of local minimum points, which appear sequentially in the waveform of the obtained second-order differential signal, as the times of the plurality of element waveforms.

The processor may obtain a difference between a second-order differential value of the local maximum point and a second-order differential value of the local minimum point for predetermined intervals of the waveform of the second-order differential signal, and extract the times of the plurality of element waveforms based on the obtained difference between the second-order differential values of each of the intervals.

The processor may extract the time of the first element waveform and the time of the second element waveform based on the differential signal, and extract a time of a third element waveform based on the fixed value.

The processor may determine a predetermined time value as the time of the third element waveform, or determine a value, obtained by adding a predetermined reference value to the time of the first element waveform or the time of the second element waveform, as the time of the third element waveform.

The predetermined time value or the predetermined reference value may include at least one of a general value for a plurality of users or a personalized value for a specific user.

The personalized value for a specific user may be obtained by analyzing the waveform of the pulse wave signal measured during a stable state.

The processor may estimate bio-information including one or more of blood pressure, vascular age, arterial stiffness, aortic pressure waveform, vascular compliance, stress index, and fatigue level.

A method of estimating bio-information may include obtaining a pulse wave signal from a user; extracting components of a plurality of element waveforms which constitute a waveform of the pulse wave signal; and obtaining a cardiovascular feature based on the extracted components of the plurality of element waveforms, wherein a component of at least one element waveform is extracted based on a component of an adjacent element waveform.

The extracting of the components of the plurality of element waveforms may include extracting times of the plurality of element waveforms based on at least one of a differential signal of the pulse wave signal and a predetermined fixed value.

The extracting of the components of the plurality of element waveforms may include extracting an amplitude of each element waveform based on an amplitude of the pulse wave signal which corresponds to a time of each element waveform.

The extracting of the components of the plurality of element waveforms may include obtaining an amplitude of the at least one element waveform by subtracting a predetermined percentage of an amplitude of the pulse wave signal corresponding to the adjacent element waveform from an amplitude of the pulse wave signal corresponding to the at least one element waveform.

The method may include estimating bio-information based on the cardiovascular feature.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
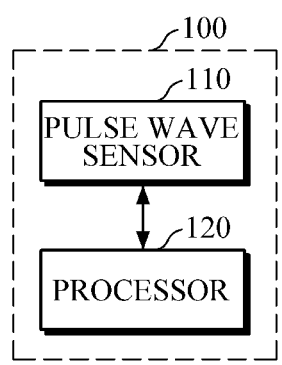
FIG. 1 is a block diagram illustrating an apparatus for estimating bio-information according to an embodiment.

Throughout the drawings and the detailed description, unless otherwise described, the same drawing reference numerals may refer to the same elements, features, and structures. The relative size and depiction of these elements, features, and structures may be exaggerated for clarity, illustration, and convenience.

DETAILED DESCRIPTION

Details of example embodiments are included in the following detailed description and drawings. Throughout the drawings and the detailed description, unless otherwise described, the same drawing reference numerals may refer to the same elements, features, and structures.

It should be understood that, although terms such as "first," "second," etc., may be used herein to describe various elements, these elements might not be limited by these terms. These terms may distinguish one element from another element. Any references to the singular form of a term may include the plural form of the term unless expressly stated otherwise. In addition, unless explicitly described to the contrary, an expression such as "comprising" or "including" may imply the inclusion of the stated elements, and might not imply the exclusion of any other elements. Also, terms such as "unit," "module," etc., may refer to a unit for processing at least one function or operation, and that may be embodied in hardware, software, or a combination thereof.

Hereinafter, embodiments of an apparatus and method for estimating bio-information will be described in detail with reference to the accompanying drawings. The apparatus for estimating bio-information according to the embodiments may be embedded in a terminal, such as a smartphone, a tablet personal computer (PC), a desktop computer, a laptop computer, and the like, or may be manufactured as an independent hardware device. In this case, the independent hardware device may be a wearable device worn on an object (OBJ), and examples of the wearable device may include a wristwatch-type wearable device, a bracelet-type wearable device, a wristband-type wearable device, a ring-type wearable device, a glasses-type wearable device, a headband-type wearable device, or the like, but the wearable device is not limited thereto.

Figure 2:
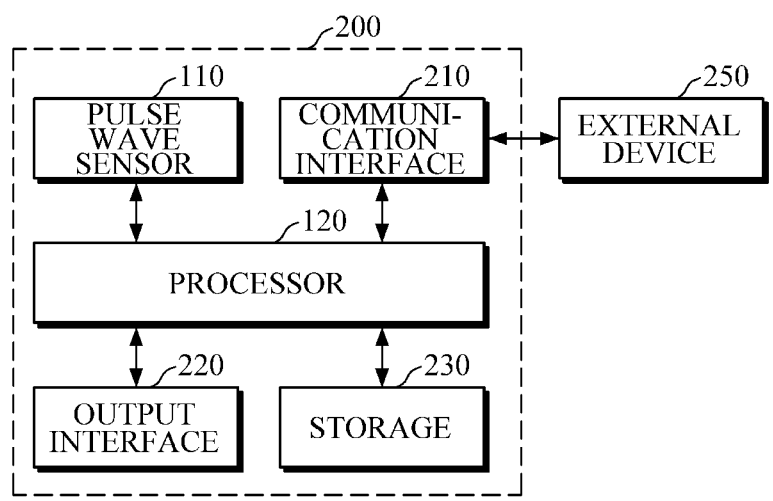
FIG. 2 is a block diagram illustrating an apparatus for estimating bio-information according to another embodiment.

FIG. 1 is a block diagram illustrating an apparatus for estimating bio-information according to an embodiment FIG. 2 is a block diagram illustrating an apparatus for estimating bio-information according to another embodiment.

Referring to FIGS. 1 and 2, the apparatuses 100 and 200 for estimating bio-information include a pulse wave sensor 110 and a processor 120.

The pulse wave sensor 110 may measure a pulse wave signal, including a photoplethysmography (PPG) signal, from an object. The pulse wave sensor 110 may include a light source configured to emit light toward the object to detect an optical signal from the object; and a detector configured to detect scattered or reflected light based on light emitted by the light source being scattered or reflected from body tissue, such as a skin surface or blood vessels of the object. The light source may include a light emitting diode (LED), a laser diode (LD), a phosphor, and the like, but is not limited thereto. The detector may include a photo diode, a photo transistor (PTr), an image sensor (e.g., a complementary metal-oxide-semiconductor (CMOS) image sensor), and the like, but is not limited thereto. The pulse wave sensor 110 may have various structures, such as a structure including a plurality of light sources and a single detector, or a structure including an array of pairs of light sources and detectors, and the like, without specific limitation.

In this case, the object may be a body part that contacts or is adjacent to the pulse wave sensor 110, and may be a body part where the pulse wave signals may be measured. For example, the object may be a skin area of the wrist which is adjacent to the radial artery, or a skin area of the body where veins or capillaries are located. However, the object is not limited thereto, and may be a distal portion of the body, such as fingers, toes, and the like, where blood vessels are densely located.

The processor 120 may be electrically connected to the pulse wave sensor 110. Based on a request for estimating bio-information, the processor 120 may control the pulse wave sensor 110, and may receive a pulse wave signal from the pulse wave sensor 110. The request for estimating bio-information may be input from a user, or may be generated at predetermined intervals. Based on receiving an electrical pulse wave signal from the pulse wave sensor 110, the processor 120 may perform preprocessing, such as filtering the pulse wave signal by removing noise, amplifying the pulse wave signal, converting the signal into a digital signal, smoothing the signal, and the like.

Based on receiving the pulse wave signal, the processor 120 may obtain cardiovascular features from the pulse wave signal, and may estimate bio-information by using the obtained cardiovascular features. In this case, bio-information may include cardiovascular information such as blood pressure, vascular age, arterial stiffness, aortic pressure waveform, vascular compliance, stress index, fatigue level, and the like. For convenience of explanation, the following description will be given using blood pressure as an example.

Generally, a variation in Mean Arterial Pressure (MAP) is proportional to cardiac output (CO) and total peripheral resistance (TPR), as represented by the following Equation 1.

$$\Delta MAP = CO \times TPR \quad \text{[Equation 1]}$$

Herein, ΔMAP denotes a difference in MAP between the left ventricle and the right atrium, in which MAP of the right atrium is generally in a range of 3 mmHg to 5 mmHg, such that the MAP in the right atrium is similar to MAP in the left ventricle or MAP of the upper arm. If absolute actual CO and TPR values are known, MAP may be obtained from the aorta or the upper arm. However, it may be difficult to estimate absolute CO and TPR values based on a bio-signal.

In an embodiment, the processor 120 may extract a feature associated with cardiac output (CO) and a feature associated with total peripheral resistance (TPR) from a bio-signal. Here, the feature associated with cardiac output (CO) may be a feature value which shows an increasing or decreasing trend in proportion to an actual CO value which relatively increases or decreases when an actual TPR value does not change significantly compared to a stable state. Further, the feature associated with total peripheral resistance (TPR) may be a feature value which shows an increasing or decreasing trend in proportion to an actual TPR value which relatively increases or decreases when an actual CO value does not change significantly compared to a stable state.

The processor 120 may extract cardiovascular features by analyzing a waveform of the measured pulse wave signal. For example, by analyzing the waveform of the pulse wave signal, the processor 120 may obtain an area of the waveform of the pulse wave signal, including heart rate information, as a feature associated with cardiac output (CO). Further, the processor 120 may obtain a ratio between an amplitude of a propagation wave and an amplitude of a first reflection wave as a feature associated with total peripheral resistance (TPR). However, the feature is not limited thereto, and the processor 120 may obtain cardiovascular features by further using time and amplitude values of a maximum point of the pulse wave signal, time and amplitude values of a minimum point of the pulse wave signal, a duration of the pulse wave signal, components of individual element waveforms which constitute the waveform of the pulse wave signal, e.g., time and amplitude values of the element waveforms, information corresponding to an internally dividing point between the obtained values, and the like.

Referring to FIG. 2, the apparatus 200 for estimating bio-information may further include a communication interface 210, an output interface 220, and a storage 230.

The communication interface 210 may communicate with an external device 250 via wired or wireless communication techniques under the control of the processor 120, and may transmit and receive various data to and from the external device 250. For example, the communication interface 210 may transmit a bio-information estimation result to the external device 250, and may receive, from the external device 250, a variety of reference information for estimating bio-information. For example, the communication interface 210 may receive a reference blood pressure measured by a cuff manometer, a bio-information estimation model, and the like. In this case, the external device 250 may include a cuff manometer, and an information processing device such as a smartphone, a tablet PC, a desktop computer, a laptop computer, and the like.

In this case, examples of the communication techniques may include Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, third generation (3G) communication, fourth generation (4G) communication, fifth generation (5G) communication, and the like. However, this is merely exemplary and is not intended to be limiting.

The output interface 220 may output results processed by the pulse wave sensor 110 and the processor 120. For example, the output interface 220 may visually output an estimated bio-information value using a display module. Alternatively, the output interface 220 may output the estimated bio-information value in a non-visual manner such as by voice, vibrations, tactile sensation, and the like, using a speaker module, a haptic module, or the like. The output interface 220 may divide a display area into two or more areas according to a setting, in which the output interface 220 may output a pulse wave signal graph used for estimating bio-information, a blood pressure estimation result, and the like, in a first area; and may output a blood pressure estimation history in the form of graphs in a second area. In this case, if an estimated blood pressure value if not within a normal range, the output interface 220 may output warning information in various manners, such as highlighting an abnormal value in red, and the like, displaying the abnormal value along with a normal range, outputting a voice warning message, adjusting a vibration intensity, and the like.

The storage 230 may store processing results of the pulse wave sensor 110 and the processor 120. Further, the storage 230 may store a variety of reference information for estimating bio-information. For example, the reference information may include reference blood pressure, an estimation equation for estimating bio-information, a bio-information estimation interval, as well as user characteristics including a user's age, sex, health condition, and the like, but is not limited thereto.

In this case, the storage 230 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 3A:
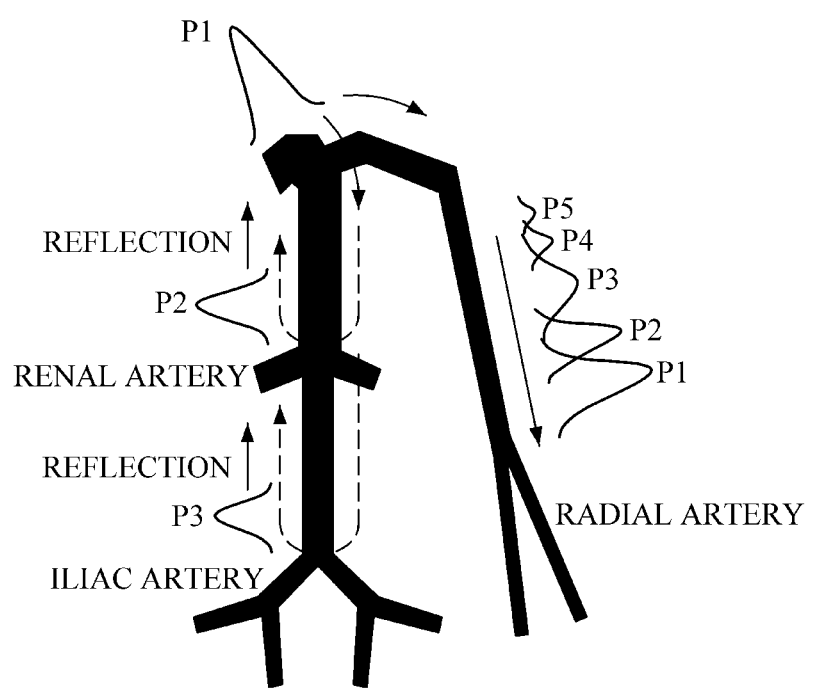
FIGS. 3A to 3C are diagrams explaining element waveforms of a pulse wave signal according to an embodiment.
Figure 3B:
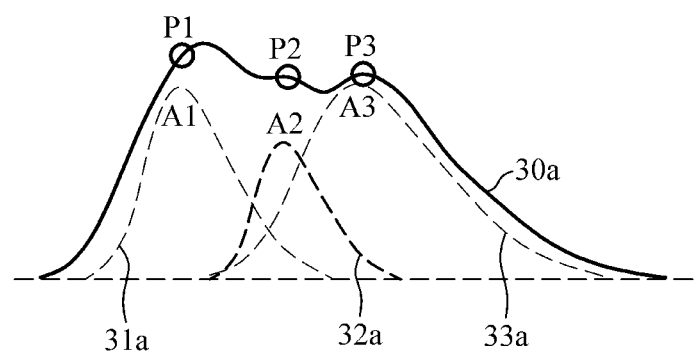
Figure 3C:
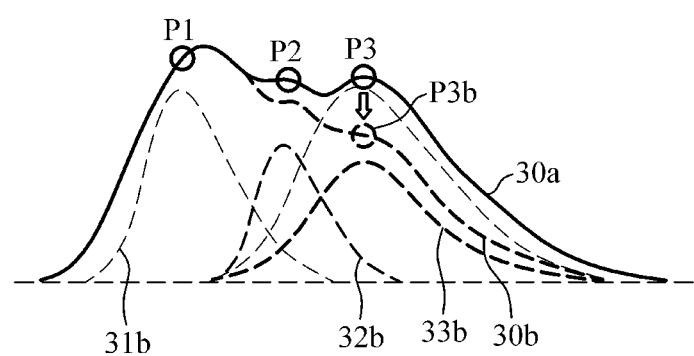

FIGS. 3A to 3C are diagrams explaining element waveforms of a pulse wave signal according to an embodiment FIGS. 4A to 4E are diagrams explaining a method of obtaining features for estimating bio-information according to an embodiment.

Generally, a pulse wave signal is formed by superposition of a propagation wave which moves from the heart to the distal end of the body or branching points in the blood vessels, and a reflection wave which returns from the distal end or the branching points. For example, referring to FIG. 3A, a pulse wave signal is generally formed by superposition of a propagation wave P1 which moves from the heart to the distal end of the body or branching points in the blood vessels by blood ejection from the left ventricle, and reflection waves P2 and P3 which return from the distal end of the body or the branching points of the blood vessels. In this case, the propagation wave P1 is related to heart characteristics, and the reflection waves P2 and P3 are related to vascular characteristics. As illustrated in FIG. 3A, the waveform of the pulse wave signal is composed of individual component waveforms, such as the propagation wave P1 which is generated by blood ejection from the left ventricle, a first reflection wave P2 which is mainly reflected from the renal arteries, a second reflection wave P3 which is mainly reflected from the iliac arteries, and the like. As described above, information related to blood pressure may be determined based on a time interval between the propagation wave and the reflection wave, which are included in the waveform of the pulse wave signal, and/or an amplitude ratio therebetween.

The processor 120 may extract components of element waveforms related to the propagation wave and the reflection wave, such as a time and an amplitude of a first element waveform, a time and an amplitude of a second element waveform, and the like, and may obtain a ratio between the extracted amplitude of the first element waveform and the extracted amplitude of the second element waveform as a feature for estimating blood pressure.

For example, referring to FIG. 3B, the processor 120 may extract an amplitude P1 of a pulse wave signal waveform 30a which is related to the first element waveform 31a, and an amplitude P2 of a pulse wave signal waveform 30a which is related to the second element waveform 32a, and may obtain a ratio between the extracted amplitudes (e.g., P2/P1) as a cardiovascular feature. In this case, usage of actual amplitudes A1, A2, and A3 of each element waveform may provide more accurate blood pressure estimation, but cardiovascular features are different for each individual, and the shape of the element waveform may change according to a current physiological condition of each individual. Accordingly, amplitude information of individual element waveforms might not be accurately derived from the superposed waveforms of the pulse wave signal.

For example, as illustrated in FIG. 3C, in the case where a pulse wave signal waveform 30b is obtained, in which the amplitude A1 of the first element waveform and the amplitude A2 of the second element waveform rarely change, and the amplitude A3 of a third element waveform is significantly reduced, it can be seen that even if there is almost no change in the amplitude A1 of the first element waveform 31b and the amplitude A2 of the second element waveform, an amplitude of an adjacent element waveform, e.g., the third element waveform 33b, which is superimposed on the second element waveform 32b, is reduced such that the amplitude P2 of the pulse wave signal waveform 30b, which is related to the second element waveform, is also reduced. As described above, when the amplitudes P1 and P2 of the pulse wave signal waveforms, which are related to individual element waveforms, are used as amplitude information of the propagation wave and the reflection waves, distortion of feature values, which are obtained for estimating blood pressure, may occur as the amplitudes of the adjacent element waveforms are changed.

Accordingly, in an embodiment, when deriving amplitude information related to individual element waveforms, the processor 120 may obtain a value approximate to an actual value by considering amplitudes of the adjacent element waveforms before and/or after the individual element waveforms. For example, referring to FIG. 4A, the processor 120 may first extract amplitudes P1, P2, and P3 of the pulse wave signal which are related to each element waveform, and then the processor 120 may correct an amplitude of the pulse wave signal, which is related to a specific element waveform, based on amplitudes of the pulse wave signal which are related to adjacent element waveforms before and/or after the specific element waveform. For example, the processor 120 may eliminate an effect of superposition of element waveforms by subtracting a predetermined percentage of the amplitude P3 of the pulse wave signal, related to the adjacent third element waveform, from the amplitude P2 of the pulse wave signal related to the second element waveform, such that the processor 120 may obtain a value approximate to an actual amplitude of the second element waveform.

The following Equation 2 represents an example of obtaining, as a feature f, a ratio between the corrected amplitude (P2−αP3) of the second element waveform and the amplitude P1 of the first element waveform. However, this is merely an example, and the feature f may be obtained by considering user characteristics, whether other additional information is used to obtain features, the additional information, types of bio-information, and the like.

$$f=(P2-\alpha P3)/P1 \quad \text{[Equation 2]}$$

Herein, α denotes a predetermined fixed value, and may be set based on various phases of change of blood pressure, e.g., based on changes of blood pressure measured in a stable state and after aerobic exercise and anaerobic exercise; and α may be a general value for a plurality of users. However, α is not limited thereto, and may be a personalized value which is adjusted for a specific user by calibration performed once at an initial time or regularly.

Figure 4A:
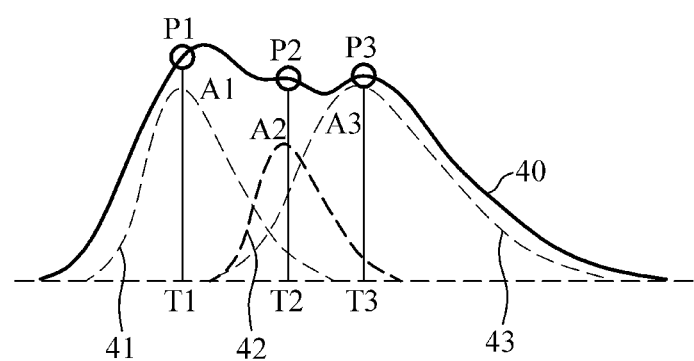
FIGS. 4A to 4E are diagrams explaining a method of obtaining features for estimating bio-information according to an embodiment.
Figure 4B:
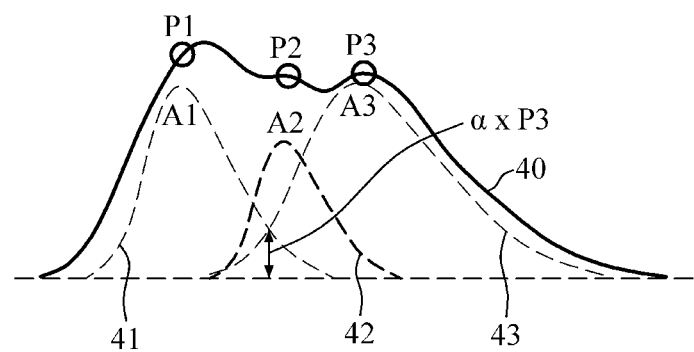

In addition, when obtaining an amplitude component of each element waveform, the processor 120 may obtain a position of each element waveform, i.e., a time component indicating a time each element waveform appears, and may obtain an amplitude at a point, corresponding to a time of each element waveform, as an amplitude component of each element waveform from the waveform of the pulse wave signal. Referring to FIGS. 4A and 4B, the processor 120 may detect a time T1 of a first element waveform 41, a time T2 of a second element waveform 42, and a time T3 of a third element waveform. Based on obtaining the time components T1, T2, and T3 of the element waveforms 41, 42, and 43, the processor 120 may obtain amplitudes P1, P2, and P3 at points, corresponding to the times T1, T2, and T3 respectively, as amplitude components of the element waveforms 41, 42, and 43.

Figure 4C:
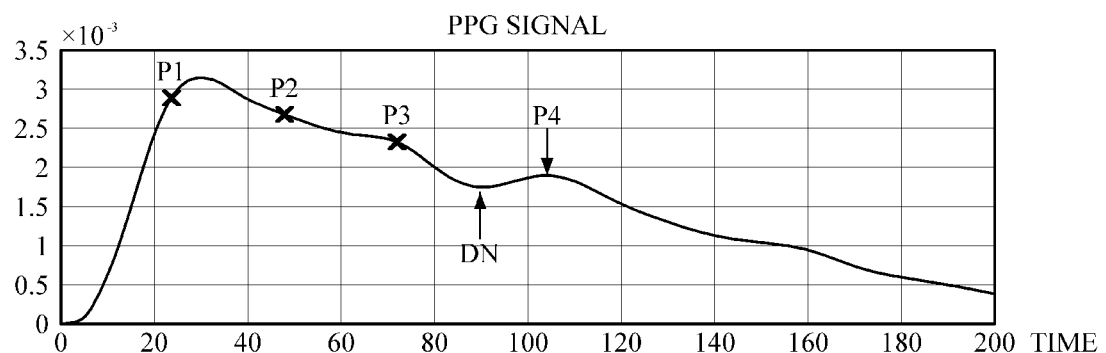
Figure 4C:
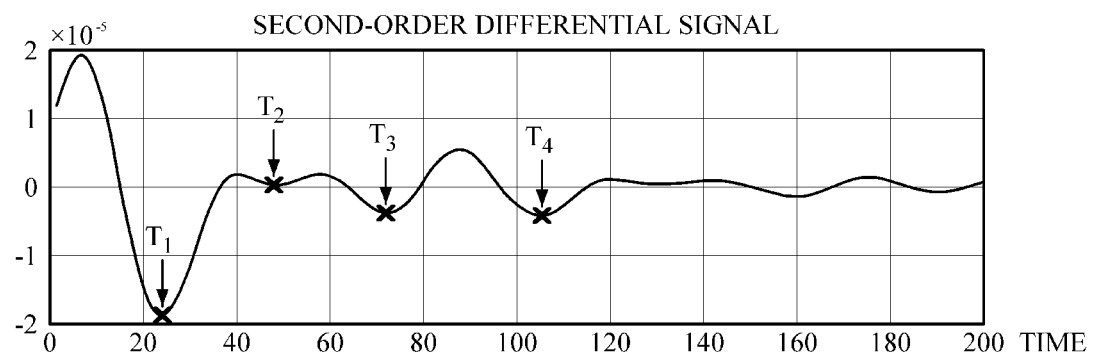

For example, the processor 120 may derive a differential signal of the pulse wave signal, and may obtain components of each element waveform by analyzing a local minimum point and/or a local maximum point of the differential signal. FIG. 4C illustrates a PPG signal (upper view) and a second-order differential signal (lower view) obtained by second-order differentiation of the PPG signal. However, differentiation is not limited to second-order differentiation. As described above, the processor 120 may obtain the second-order differential signal of the pulse wave signal, and may detect a position, at which a local minimum point occurs, in the obtained second-order differential signal. The processor 120 may obtain times T1, T2, T3, and T4 of four local minimum points, which are sequentially detected, as time components of the element waveforms. Further, the processor 120 may obtain amplitudes P1, P2, P3, and P4 at points, corresponding to the time components T1, T2, T3, and T4 of the element waveforms, as amplitude components of each element waveform from the PPG waveform (upper view).

In another example, by using concavity and/or convexity of the waveform of the pulse wave signal, the processor 120 may obtain time components of each element waveform. As described above, the processor 120 may obtain positions of three local minimum points, which are sequentially detected, as time components of the first, second, and third element waveforms from the second-order differential signal. However, the waveform of the PPG signal of FIG. 4C has a shape which is very slightly convex upward due to a non-ideal and subtle change in the waveform occurring in the vicinity of the amplitude P2, such that the position at T2 becomes a local minimum point of the second-order differential signal, and is erroneously detected as the time of the second element waveform. That is, accurate positions of the first, second, and third element waveforms in the PPG signal of FIG. 4C may be T1, T3, and T4 of the second-order differential signal.

Figure 4D:
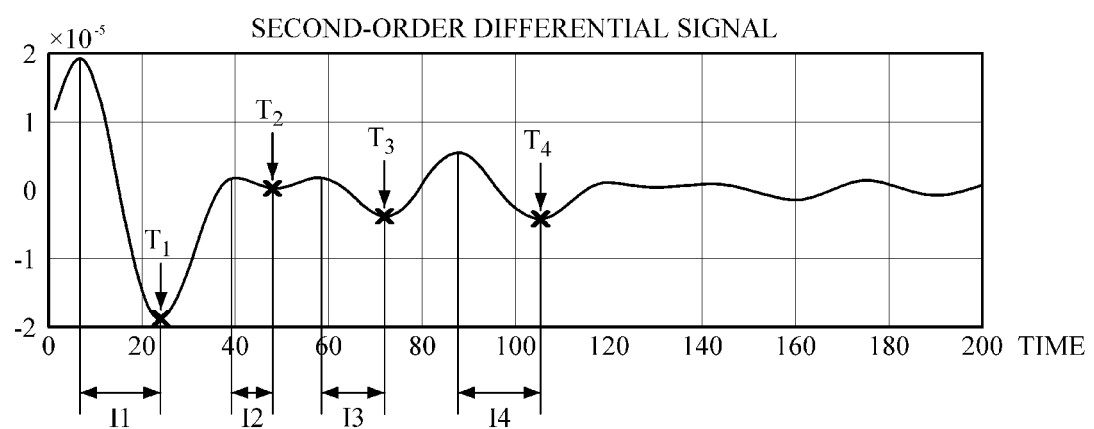

Referring to FIG. 4D, in order to analyze the concavity and/or convexity properties of the waveform of the pulse wave signal, the processor 120 may obtain a second-order differential signal of the pulse wave signal, and may divide the obtained second-order differential signal into a plurality of intervals I1, I2, I3, and I4. The number of intervals is not specifically limited, and may be set to a number equal to or greater than the number of element waveforms to be obtained. In this case, the intervals may be, for example, time intervals between times of local maximum points and times of local minimum points which appear sequentially on a time axis of the second-order differential signal. However, the interval is not limited thereto, and may be a pre-defined successive time interval.

The processor 120 may calculate a convexity-concavity degree (CCD) value for each of the intervals, and may obtain a time component of each element waveform based on the calculated CCD value. For example, the processor 120 may obtain a difference between a magnitude of a local maximum point and a magnitude of a local minimum point in each interval as a CCD value of each interval. In this case, the magnitudes of the local maximum point and the local minimum point may be second-order differential values corresponding to the local maximum point and the local minimum point. The processor 120 may determine a first interval I1, a fourth interval I4, and a third interval I3 in the order of magnitude of CCD values, and may obtain times T1, T4, and T3 of local minimum points of the determined intervals I1, I4, and I3. The processor 120 may obtain the obtained times T1, T4, and T3 of the local minimum points as time components of the first, second, and third element waveforms in chronological order.

Further, when dividing the waveform of the second-order differential signal into predetermined intervals, some intervals may be integrated into a single interval by considering characteristics of the waveform and the like. In the case where high-frequency components, which fluctuate irregularly, are contained in the obtained pulse wave signal due to non-ideal factors, the second-order differential signal may fluctuate unstably. In this case, based on a fluctuation of the waveform at two or more points in the intervals divided from the second-order differential signal, the processor 120 may integrate the divided two or more intervals. However, the processor 120 is not limited thereto, and may also provide a filtering effect to further smooth the original pulse wave signal or the second-order differential signal.

Figure 4E:
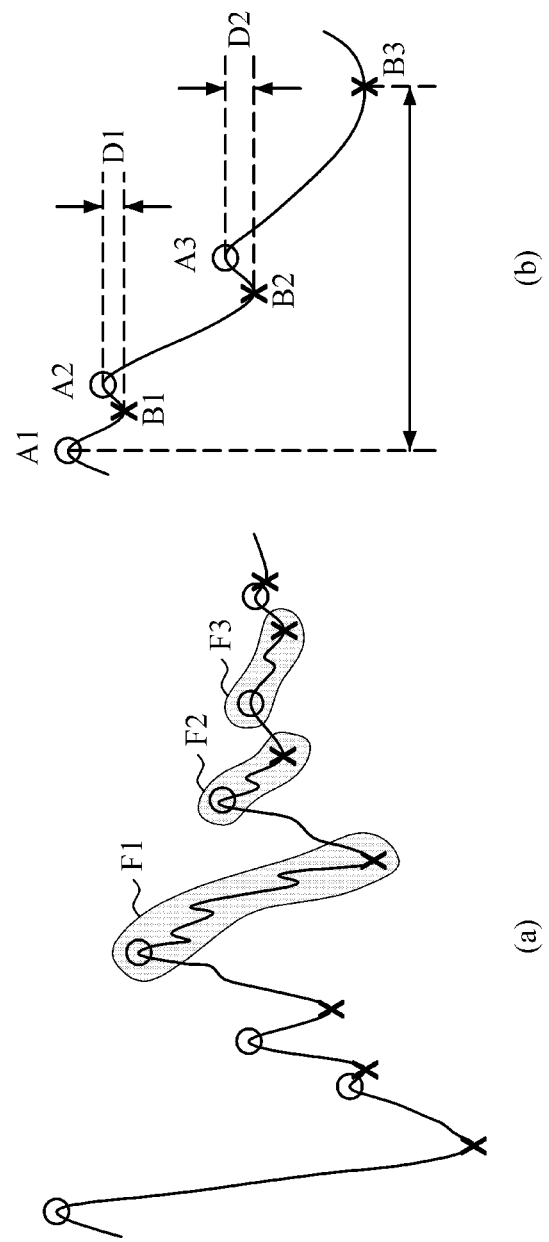

For example, referring to FIG. 4E, (a) illustrates an example in which significant fluctuations occur in intervals F1, F2, and F3 of the second-order differential signal due to an unstable waveform. As illustrated herein, if the second-order differential signal has intervals F1, F2, and F3 which fluctuate significantly, the processor 120 may integrate the significantly fluctuating intervals F1, F2, and F3 into a single interval according to predetermined criteria. Further, (b) of FIG. 4E illustrates an example for explaining a method of integrating fluctuating intervals of the second-order differential signal. By sequentially dividing a first local maximum point A1 and local minimum point B1 as a first interval, a second local maximum point A2 and local minimum point B2 as a second interval, and a third local maximum point A3 and local minimum point B3 as a third interval, the processor 120 may determine whether to integrate an interval, currently to be divided, into a previous interval.

For example, when dividing the first interval and then dividing the second interval, the processor 120 may calculate a difference between a second-order differential value of the local maximum point A2 of the second interval and a second-order differential value of the local minimum point B1 of the first interval as a fluctuation D1 of the second interval. Then, the processor 120 may compare the calculated fluctuation D1 of the second interval with a predetermined reference value; and if the fluctuation D1 of the second interval is less than the reference value, the processor 120 may integrate the second interval into the first interval. Likewise, when dividing the third interval, the processor 120 may calculate a difference between a second-order differential value of the local maximum point A3 of the third interval and a second-order differential value of the local minimum point B2 of the second interval as a fluctuation D2 of the third interval. Then, if the fluctuation D2 of the third interval is less than the reference value, the processor 120 may integrate the third interval into the second interval.

If both the fluctuation D1 of the second interval and the fluctuation D2 of the third interval are less than a threshold value, the processor 120 may integrate the first interval, the second interval, and the third interval into a single interval, and a local maximum point and a local minimum point of the integrated interval may be the local maximum point A1 of the first interval and the local minimum point B3 of the last interval respectively before integration. Here, the predetermined reference value may be set by considering a measurement state of the pulse wave signal, device performance, and the like. For example, the reference value may be a value obtained by multiplying a first value for considering a case, in which a bio-signal may be measured differently according to measurement conditions, by a second value which is preset by considering device performance, and the like. In this case, the first value may be a CCD value calculated for a first constituent pulse which is obtained relatively stably, but is not limited thereto.

Further, a method of integrating a predetermined interval is not limited to the above example. For example, at least some intervals, e.g., intervals for obtaining a time component of a third element waveform, are divided into predetermined time intervals, and all the subtle local minimum and/or local maximum points in each time interval may be integrated.

In another example, the processor 120 may obtain a time component of an element waveform by using a predetermined fixed value. In this case, the fixed value may be a general value for a plurality of users, or a personalized value for each user. In this case, the personalized value for a specific user may be a value obtained by analyzing the waveform of a pulse wave signal which is measured at a stable time when the user is in a stable state.

For example, the processor 120 may extract time components of the first element waveform and the second element waveform as described above, and may use a fixed value as a time component of the third element waveform. Alternatively, upon obtaining the time component of the first element waveform or the second element waveform, the processor 120 may use a time value, obtained by adding a predetermined reference value to the time of the first element waveform or the time of the second element waveform, as a time component of the third element waveform.

The processor 120 may estimate bio-information based on features obtained by analyzing the waveform of the pulse wave signal. In addition to the obtained cardiovascular feature, i.e., a ratio between the amplitude of the first element waveform and the amplitude of the second element waveform, the processor 120 may further obtain various features including an area of the waveform of the pulse wave signal, and may estimate bio-information by using the predetermined bio-information estimation model.

Figure 5:
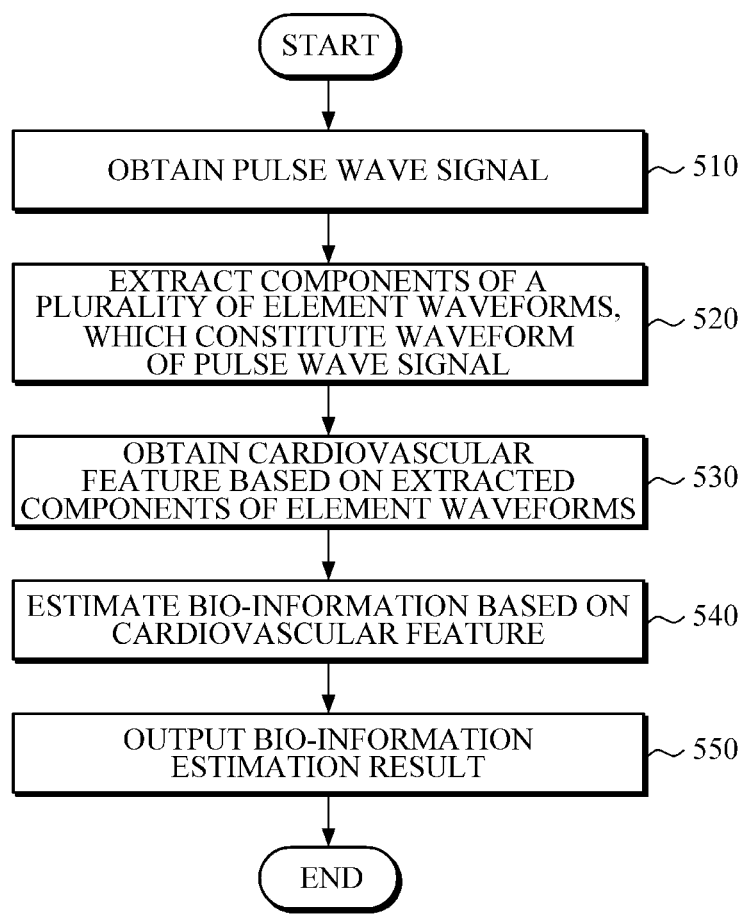
FIG. 5 is a flowchart illustrating a method of estimating bio-information according to an embodiment.

FIG. 5 is a flowchart illustrating a method of estimating bio-information according to an embodiment. The method of FIG. 5 may be a method of estimating bio-information which is performed by the apparatuses 100 or 200 for estimating bio-information as described above in association with FIG. 1 or FIG. 2. Various embodiments thereof are described above in detail, such that the description thereof will be briefly made below.

Based on receiving a request for estimating bio-information, the apparatuses 100 and 200 for estimating bio-information may obtain a pulse wave signal from an object in operation 510. The apparatuses 100 and 200 for estimating bio-information may provide a user with a user interface, and may receive the request for estimating bio-information which is input by the user via the user interface. Alternatively, the apparatuses 100 and 200 for estimating bio-information may communicate with an external device, and may receive the request for estimating bio-information from the external device.

Based on obtaining the pulse wave signal, the apparatuses 100 and 200 for estimating bio-information may extract components of a plurality of element waveforms, which constitute the waveform of the pulse wave signal, by analyzing the waveform of the obtained pulse wave signal in operation 520. The waveform of the pulse wave signal is generally formed by superposition of a propagation wave, which moves from the heart to the distal end of the body or branching points in the blood vessels by blood ejection from the left ventricle, and reflection waves which return from the distal end of the body or the branching points of the blood vessels. By analyzing the waveform of the pulse wave signal, the apparatuses 100 and 200 for estimating bio-information may extract components of individual element waveforms related to the propagation wave and/or the reflection wave, e.g., time and amplitude information of the propagation wave and/or the reflection wave.

For example, the apparatuses 100 and 200 for estimating bio-information may derive a differential signal of the pulse wave signal, and may extract components of each element waveform by analyzing the waveform of the differential signal. For example, the apparatuses 100 and 200 for estimating bio-information may detect a local minimum point from the waveform of the second-order differential signal of the pulse wave signal, and may obtain times of local minimum points, which are detected sequentially in chronological order, as time components of element waveforms related to the propagation wave, the first reflection wave, and the second reflection wave respectively.

In another example, the apparatuses 100 and 200 for estimating bio-information may obtain time components of each element waveform by analyzing concavity and/or convexity of the waveform of the pulse wave signal. For example, in the case where the waveform of the pulse wave signal has a shape which is slightly convex upward at an abnormal position due to motion noise, and the like, during measurement of the pulse wave signal, that position may be erroneously detected as a position of the waveform. Accordingly, the apparatuses 100 and 200 for estimating bio-information may calculate a CCD value based on the concavity and/or convexity properties of the waveform of the pulse wave signal, i.e., the second-order differential signal, and may extract time components of the element waveform based on the calculated CCD value.

In another example, the apparatuses 100 and 200 for estimating bio-information may also obtain time components of the element waveforms by using a predetermined fixed value. In this case, the fixed value may be a general value for a plurality of users or a personalized value for each user. In this case, the personalized value for a specific user may be a value obtained by analyzing the waveform of the pulse wave signal which is measured at a stable time when the user is in a stable state.

Based on obtaining the time components of the element waveforms, the apparatuses 100 and 200 for estimating bio-information may obtain amplitude values at points, corresponding to the times obtained from the waveform of the pulse wave signal, as amplitude components of each element waveform. In this case, in order to reduce distortion of the amplitude of the pulse wave signal waveform, which is caused by superposition of element waveforms, the apparatuses 100 and 200 for estimating bio-information may correct the amplitude of the pulse wave signal by considering amplitude components of adjacent element waveforms when obtaining an amplitude component of a specific element waveform. For example, an amplitude of the pulse wave signal, which is related to the second element waveform, may change according to an amplitude of the pulse wave signal related to the third element waveform. Accordingly, by removing a predetermined percentage of the amplitude component of the third element waveform, an effect of superposition of the third element waveform on the amplitude component of the second element waveform may be reduced.

Based on the extracting the components, the apparatuses 100 and 200 for estimating bio-information may obtain cardiovascular features based on the extracted components of the element waveforms in operation 530. In this case, the cardiovascular features may include a feature associated with cardiac output and a feature associated with total peripheral resistance. For example, the apparatuses 100 and 200 for estimating bio-information may obtain a ratio between an amplitude of a first element waveform and an amplitude of a second element waveform as the feature associated with total peripheral resistance. However, the feature is not limited thereto, and the apparatuses 100 and 200 for estimating bio-information may also obtain an area of the waveform of the pulse wave signal as the feature associated with cardiac output, and may obtain a variety of additional information by analyzing the waveform of the pulse wave signal.

Based on extracting the cardiovascular features, the apparatuses 100 and 200 for estimating bio-information may estimate bio-information based on the extracted cardiovascular features in operation 540. Based on extracting various cardiovascular features in operation 530, the apparatuses 100 and 200 for estimating bio-information may estimate bio-information by using a pre-defined bio-information estimation model.

Based on estimating the bio-information, the apparatuses 100 and 200 for estimating bio-information may output a bio-information estimation result in operation 550. The apparatuses 100 and 200 for estimating bio-information may provide the bio-information estimation result, a user's health information analyzed by using the estimation result, and the like, for the user by using various output devices such as a display, a haptic device, a speaker, and the like.

Figure 6:
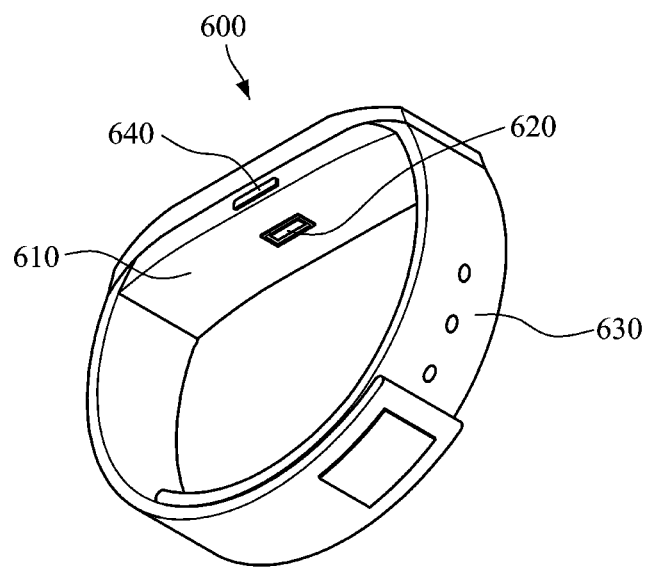
FIG. 6 is a diagram illustrating a wearable device according to an embodiment.

FIG. 6 is a diagram illustrating a wearable device according to an embodiment. The aforementioned various embodiments of the apparatus for estimating bio-information may be mounted in a smart watch worn on a wrist or a smart band-type wearable device, as illustrated in FIG. 6.

Referring to FIG. 6, the wearable device 600 includes a main body 610 and a strap 630.

The main body 610 may be formed to have various shapes, and may include modules which are mounted inside or outside of the main body 610 to perform the aforementioned function of estimating bio-information, as well as various other functions. A battery may be embedded in the main body 610 or the strap 630 to supply power to various modules of the wearable device 600.

The strap 630 may be connected to the main body 610. The strap 630 may be flexible so as to be bent around a user's wrist. The strap 630 may be bent in a manner that allows the strap 630 to be detached from the user's wrist or may be formed as a band that is non-detachable. Air may be injected into the strap 630 or an airbag may be included in the strap 630, so that the strap 630 may have elasticity according to a change in pressure applied to the wrist, and the change in pressure of the wrist may be transmitted to the main body 610.

The main body 610 may include a pulse wave sensor 620 for measuring a bio-signal. The pulse wave sensor 620 may be mounted on a rear surface of the main body 610, which may contact the upper portion of a user's wrist, and may include a light source for emitting light toward the skin of the wrist and a detector for detecting light scattered or reflected from the object.

A processor may be mounted in the main body 610. The processor may be electrically connected to various modules, mounted in the wearable device 600, to control operations thereof.

Further, the processor may estimate bio-information by using a pulse wave signal measured by the pulse wave sensor 620. The processor may obtain cardiovascular features from the pulse wave signal, and may estimate bio-information by using the obtained features. The processor may obtain cardiovascular features by analyzing the waveform of the pulse wave signal. For example, the processor may extract times and amplitudes of element waveforms which constitute the waveform of the pulse wave signal, and may obtain cardiovascular features based on the extracted time and/or amplitude components of each element waveform. In this case, in order to minimize distortion of the amplitude of the pulse wave signal waveform, which is caused by superposition of the element waveforms, the processor may extract an amplitude component of a specific element waveform by considering amplitude components of adjacent element waveforms.

Further, the main body 610 may further include a contact pressure sensor for measuring contact pressure between an object and the pulse wave sensor 620 while a pulse wave signal is measured when the object is in contact with the pulse wave sensor 620. In this case, the processor may monitor a contact state of the object based on the contact pressure measured by the contact pressure sensor, and may provide guide information on a contact position and/or a contact state for a user through a display.

Further, the main body 610 may include a storage which stores a processing result of the processor and a variety of information. In this case, the variety of information may include reference information related to estimating bio-information, as well as information associated with functions of the wearable device 600.

In addition, the main body 610 may also include an input component 640 which receives a user's control command, and transmits the received control command to the processor. The input component 640 may include a power button to input a command to turn on or turn off the wearable device 600.

A display may be mounted on a front surface of the main body 610, and may include a touch panel for receiving a touch input. The display may receive a touch input from a user, may transmit the received touch input to the processor, and may display a processing result of the processor.

For example, the display may display a bio-information estimation result. In this case, along with the estimation result, the display may display additional information such as a bio-information estimation date, a health condition, and the like. In this case, when a user requests detailed information by operating the manipulator 640 or by performing touch input on the display, the display may display detailed information in various manners.

Moreover, a communication interface, provided for communication with an external device such as a user's mobile terminal, may be mounted in the main body 610. The communication interface may transmit a bio-information estimation result to an external device, e.g., a user's smartphone, to display the estimation result to the user. However, the communication interface is not limited thereto, may transmit and receive a variety of information.

Figure 7:
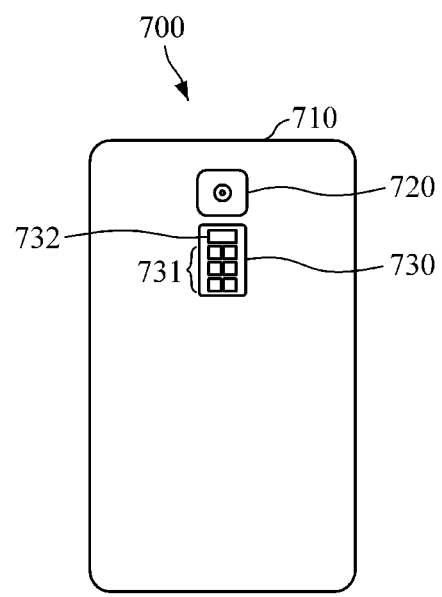
FIG. 7 is a diagram illustrating a smart device according to an embodiment.

FIG. 7 is a diagram illustrating a smart device, to which embodiments of an apparatus for estimating bio-information are applied. In this case, the smart device may be a smartphone, a tablet PC, and the like.

Referring to FIG. 7, the smart device 700 includes a main body 710 and a pulse wave sensor 730 mounted on one surface of the main body 710. In this case, the pulse wave sensor 730 may include one or more light sources 731 and a detector 732. As illustrated in FIG. 7, the pulse wave sensor 730 may be mounted on a rear surface of the main body 710, but is not limited thereto, and may be configured in combination with a fingerprint sensor or a touch panel mounted on a front surface of the main body 710.

In addition, a display may be mounted on a front surface of the main body 710. The display may visually display a bio-information estimation result and the like. The display may include a touch panel, and may receive a variety of information input through the touch panel and transmit the received information to the processor.

Moreover, an image sensor 720 may be mounted in the main body 710. When a user's finger approaches the pulse wave sensor 730 to measure a pulse wave signal, the image sensor 720 may capture an image of the finger and may transmit the captured image to the processor. In this case, based on the image of the finger, the processor may identify a relative position of the finger with respect to an actual position of the pulse wave sensor 730, and may provide the relative position of the finger to the user through the display, so as to guide measurement of pulse wave signals with improved accuracy.

As described above, the processor may estimate bio-information based on the pulse wave signal measured by the pulse wave sensor 730. In this case, as described above, the processor may obtain components, e.g., times and amplitudes, of individual element waveforms related to the propagation wave and the reflection wave from the pulse wave signal, and may obtain cardiovascular features based on the obtained components of the element waveforms. In this case, by eliminating an effect of superposition of the element waveforms, the processor may consider components of adjacent element waveforms when obtaining a component of a specific element waveform.

The main body 710 of the smart device 700 may include a storage which stores reference information and the like for operation of the smart device 700, including other information input from a user, information obtained by various sensors, information processed by the processor, and other reference information required for estimating bio-information.

Further, the main body 710 of the smart device 700 may include a communication interface for communication with various external devices, e.g., a wearable device, a desktop computer, a laptop computer, a tablet PC, a cuff manometer, a smart device of another user, and the like. The processor may control the communication interface to transmit and receive a bio-information estimation result, a variety of reference information, and the like, to and from another external device.

The embodiments of the present disclosure can be realized as computer-readable code stored on a non-transitory computer-readable medium. The computer-readable medium may be any type of recording device in which data is stored in a computer-readable manner.

Examples of the computer-readable medium include a ROM, a RAM, a CD-ROM, a magnetic tape, a floppy disc, an optical data storage, and a carrier wave (e.g., data transmission through the Internet). The computer-readable medium may be distributed over a plurality of computer systems connected to a network so that computer-readable code is written thereto and executed therefrom in a decentralized manner. Also, functional programs, code, and code segments for implementing the embodiments of the present disclosure should be readily construed by programmers of ordinary skill in the art, to which the present disclosure pertains.

The present disclosure has been described herein with regard to preferred embodiments. However, it should be apparent to those skilled in the art that various changes and modifications can be made without departing from the scope of the present disclosure. Thus, it is clear that the above-described embodiments are illustrative in all aspects and are not intended to limit the present disclosure.

What is claimed is:

1. An apparatus for estimating bio-information, the apparatus comprising:
 a processor configured to:
  obtain a pulse wave signal from a user using a pulse wave sensor;
  extract components of a plurality of element waveforms which constitute a waveform of the pulse wave signal;
  obtain a cardiovascular feature based on the extracted components of the plurality of element waveforms,
  wherein the processor is configured to extract a component of at least one element waveform based on a component of an adjacent element waveform, and
  estimate bio-information including one or more of blood pressure, vascular age, arterial stiffness, aortic pressure waveform, vascular compliance, stress index, and fatigue level,
  wherein the processor obtains the cardiovascular feature of the plurality of element waveforms further based on a predetermined fixed value, the
  predetermined fixed value corresponding to a change between a condition of anaerobic activity and stable cardiovascular condition; and
 further comprising an image sensor for taking an image of the user as the user contacts the pulse wave sensor, and the processor further identifies a difference in position between a point of user contact and the pulse wave sensor in the image, and based on the difference in position provides re-positioning instructions to the user to improve positioning between the user and the pulse wave sensor to improve accuracy of the estimated bio-information; and
 further comprising a display to output the re-positioning instructions to the user to instruct the user to move the point of user contact,
 wherein the processor extracts times of the plurality of element waveforms based on a differential signal of the pulse wave signal,
 wherein the processor extracts an amplitude of each element waveform based on an amplitude of the pulse wave signal which corresponds to a time of each element waveform, and
 wherein the predetermined fixed value comprises a predetermined percentage and wherein processor is further configured to:
 subtract the predetermined percentage of an amplitude of the pulse wave signal corresponding to the adjacent element waveform from an amplitude of the pulse wave signal corresponding to the at least one element waveform; and
 obtain an amplitude of the at least one element waveform.

2. The apparatus of claim 1, wherein the components of the plurality of element waveforms comprise a time and an amplitude of a first element waveform related to a propagation wave, and a time and an amplitude of a second element waveform related to a reflection wave.

3. The apparatus of claim 2, wherein the cardiovascular feature comprises a ratio between the amplitude of the first element waveform and the amplitude of the second element waveform.

4. The apparatus of claim 1, wherein the predetermined percentage is a general value obtained from a plurality of users or a personalized value obtained from a specific user in a stable state.

5. The apparatus of claim 1, wherein the processor is further configured to:
 obtain a second-order differential signal of the pulse wave signal; and
 extract the components of the plurality of element waveforms by analyzing a local minimum point or a local maximum point of a waveform of the obtained second-order differential signal.

6. The apparatus of claim 5, wherein the processor is further configured to:

extract times of local minimum points, which appear sequentially in the waveform of the obtained second-order differential signal, as the times of the plurality of element waveforms.

7. The apparatus of claim 5, wherein the processor is further configured to:
obtain a difference between a second-order differential value of the local maximum point and a second-order differential value of the local minimum point for predetermined intervals of the waveform of the second-order differential signal; and
extract the times of the plurality of element waveforms based on the obtained difference between the second-order differential values of each of the intervals.

8. An apparatus for estimating bio-information, the apparatus comprising:
a processor configured to:
obtain a pulse wave signal from a user using a pulse wave sensor;
extract components of a plurality of element waveforms which constitute a waveform of the pulse wave signal;
obtain a cardiovascular feature based on the extracted components of the plurality of element waveforms,
wherein the processor is configured to extract a component of at least one element waveform based on a component of an adjacent element waveform, and
estimate bio-information including one or more of blood pressure, vascular age, arterial stiffness, aortic pressure waveform, vascular compliance, stress index, and fatigue level,
wherein the processor obtains the cardiovascular feature of the plurality of element waveforms further based on a predetermined fixed value, the predetermined fixed value corresponding to a change between a condition of anaerobic activity and stable cardiovascular condition; and
further comprising an image sensor for taking an image of the user as the user contacts the pulse wave sensor, and the processor further identifies a difference in position between a point of user contact and the pulse wave sensor in the image, and based on the difference in position provides re-positioning instructions to the user to improve positioning between the user and the pulse wave sensor to improve accuracy of the estimated bio-information; and
further comprising a display to output the re-positioning instructions to the user to instruct the user to move the point of user contact,
wherein the processor extracts times of the plurality of element waveforms based on a differential signal of the pulse wave signal,
wherein the processor is further configured to:
extract a time of a first element waveform and a time of a second element waveform based on the differential signal; and
extract a time of a third element waveform based on the predetermined fixed value.

9. The apparatus of claim 8, wherein the processor is further configured to:
determine a predetermined time value as the time of the third element waveform; or
determine a value, obtained by adding a predetermined reference value to the time of the first element waveform or the time of the second element waveform, as the time of the third element waveform.

10. The apparatus of claim 9, wherein the predetermined time value or the predetermined reference value comprises at least one of a general value for a plurality of users or a personalized value for a specific user.

11. The apparatus of claim 10, wherein the personalized value for a specific user is obtained by analyzing the waveform of the pulse wave signal measured during a stable state.

12. A method of estimating bio-information, the method comprising:
obtaining a pulse wave signal from a user using a pulse wave sensor;
extracting components of a plurality of element waveforms which constitute a waveform of the pulse wave signal;
obtaining a cardiovascular feature based on the extracted components of the plurality of element waveforms,
wherein a component of at least one element waveform is extracted based on a component of an adjacent element waveform,
estimating bio-information based on the cardiovascular feature,
wherein obtaining the cardiovascular feature of the plurality of element waveforms is further based on a predetermined fixed value, the predetermined fixed value corresponding to a change between a condition of anaerobic activity and stable cardiovascular condition, and
taking an image of the user as the user contacts the pulse wave sensor, and identifying a difference in position between a point of user contact and the pulse wave sensor in the image, and based on the difference in position,
providing re-positioning instructions to the user to improve positioning between the user and the pulse wave sensor to improve accuracy of estimating the bio-information,
displaying the re-positioning instructions to the user on a display device to instruct the user to move the point of user contact,
extracting times of the plurality of element waveforms based on a differential signal of the pulse wave signal,
extracting an amplitude of each element waveform based on an amplitude of the pulse wave signal which corresponds to a time of each element waveform, and
wherein the predetermined fixed value comprises a predetermined percentage; and
subtracting the predetermined percentage of an amplitude of the pulse wave signal corresponding to the adjacent element waveform from an amplitude of the pulse wave signal corresponding to the at least one element waveform; and
obtaining an amplitude of the at least one element waveform.

13. A method of estimating bio-information of a user, the method comprising:
obtaining a pulse wave signal of the user using a pulse wave sensor;
extracting a first amplitude of the pulse wave signal corresponding to a first element waveform;
extracting a second amplitude of the pulse wave signal corresponding to a second element waveform;
extracting a third amplitude of the pulse wave signal corresponding to a third element waveform that is adjacent to the second element waveform;
obtaining a corrected amplitude of the pulse wave signal corresponding to the second element waveform, based on the third amplitude;

obtaining the bio-information of the user based on the first amplitude and the corrected amplitude, wherein obtaining the corrected amplitude is further based on a predetermined fixed value, the predetermined fixed value corresponding to a change between a condition of anaerobic activity and stable cardiovascular condition, and taking an image of the user as the user contacts the pulse wave sensor, and identifying a difference in position between the pulse wave sensor and a point of contact of the user based on the taken image, and based on the difference in position, providing re-positioning instructions to the user to improve positioning between the user and the pulse wave sensor to improve accuracy of the obtained bio-information, displaying re-positioning instructions to the user to move the point of user contact;

extracting times of the first element waveform, the second element waveform, and the third element waveform based on a differential signal of the pulse wave signal, extracting an amplitude of each element waveform based on an amplitude of the pulse wave signal which corresponds to a time of each element waveform, and wherein the predetermined fixed value comprises a predetermined percentage; and subtracting the predetermined percentage of an amplitude of the pulse wave signal corresponding to an adjacent element waveform from an amplitude of the pulse wave signal corresponding to the at least one element waveform; and obtaining an amplitude of the at least one element waveform.

\* \* \* \* \*